United States Patent
Gruendken et al.

(10) Patent No.: US 10,551,803 B2
(45) Date of Patent: *Feb. 4, 2020

(54) METHOD FOR ADAPTING THRESHOLD WINDOWS, CONTROL DEVICE, MEDICAL TREATMENT APPARATUS AND MEDICAL MONITORING APPARATUS

(71) Applicant: FRESENIUS MEDICAL CARE DEUTSCHLAND GMBH, Bad Homburg (DE)

(72) Inventors: Martin Gruendken, Rosbach (DE); Uwe Herrmann, Nuthetal (DE); Sabine Kipp, Bad Homburg (DE); Christine Nachbaur-Sturm, Eitorf (DE); Thomas Pusinelli, Altenstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 459 days.

This patent is subject to a terminal disclaimer.

(21) Appl. No.: 15/067,551

(22) Filed: Mar. 11, 2016

(65) Prior Publication Data

US 2016/0196401 A1 Jul. 7, 2016

Related U.S. Application Data

(63) Continuation of application No. 13/511,291, filed as application No. PCT/EP2010/007075 on Nov. 23, 2010, now Pat. No. 9,311,448.

(30) Foreign Application Priority Data

Nov. 24, 2009 (DE) .................. 10 2009 054 395

(51) Int. Cl.
 *G05B 13/02* (2006.01)
 *A61M 1/16* (2006.01)
 *A61M 1/36* (2006.01)

(52) U.S. Cl.
 CPC ......... *G05B 13/024* (2013.01); *A61M 1/1601* (2014.02); *A61M 1/3621* (2013.01); *A61M 1/3639* (2013.01); *A61M 2205/33* (2013.01)

(58) Field of Classification Search
 CPC ............. G06F 19/2406; A61M 1/3639; A61M 1/3621; A61M 2205/33
 (Continued)

(56) References Cited

U.S. PATENT DOCUMENTS

| 5,401,238 A | 3/1995 | Pirazzoli |
|---|---|---|
| 6,178,228 B1 | 1/2001 | Schol |

(Continued)

FOREIGN PATENT DOCUMENTS

| CN | 1511010 | 7/2004 |
|---|---|---|
| CN | 101489602 | 7/2009 |

(Continued)

OTHER PUBLICATIONS

PCT International Search Report from PCT/EP2010/007075, dated Mar. 31, 2011. [cited in parent application].

(Continued)

*Primary Examiner* — Leslie R Deak
(74) *Attorney, Agent, or Firm* — Fish & Richardson P.C.

(57) ABSTRACT

The present invention relates to a method of adapting of a second threshold window of at least a second measured variable depending on the change of a first threshold window of a first measured variable, wherein the adaptation is performed by the use of a control unit having been provided and/or configured therefor. The present invention further relates to a control device, a medical treatment apparatus, a medical monitoring apparatus, a digital storage means, a computer program product and a computer program.

12 Claims, 1 Drawing Sheet

(58) Field of Classification Search
USPC .... 604/4.01, 5.01, 5.04, 6.09; 210/645, 646, 210/739
See application file for complete search history.

(56) References Cited

U.S. PATENT DOCUMENTS

| | | |
|---|---|---|
| 6,241,661 B1 | 6/2001 | Schluess et al. |
| 2002/0156352 A1 | 10/2002 | Eggers |
| 2004/0032341 A1 | 2/2004 | Brenner et al. |
| 2009/0289799 A1 | 11/2009 | Tivig et al. |
| 2009/0292236 A1 | 11/2009 | Kleinekofort |
| 2010/0179467 A1 | 7/2010 | Gunther et al. |
| 2011/0106466 A1 | 5/2011 | Furmanski et al. |

FOREIGN PATENT DOCUMENTS

| | | |
|---|---|---|
| DE | 19810069 A1 | 9/1999 |
| DE | 10013666 A1 | 10/2001 |
| DE | 10045097 A1 | 4/2002 |
| DE | 10114383 A1 | 10/2002 |
| DE | 102006032815 A1 | 1/2008 |
| DE | 102007026010 A1 | 12/2008 |
| EP | 0909551 | 4/1999 |
| JP | H06-501188 | 2/1994 |
| JP | 07-008553 A | 1/1995 |
| JP | H11-338534 | 12/1999 |
| JP | 2000-00300 A | 1/2000 |
| JP | 2001-087379 A | 4/2001 |
| JP | 2008173469 A | 7/2008 |
| JP | 2008525087 | 7/2008 |

OTHER PUBLICATIONS

Japanese Search Report by Registered Searching Organization in Japanese Application No. 2012-539235, dated Aug. 25, 2014, 11 pages (with English translation).

METHOD FOR ADAPTING THRESHOLD WINDOWS, CONTROL DEVICE, MEDICAL TREATMENT APPARATUS AND MEDICAL MONITORING APPARATUS

CROSS REFERENCE TO RELATED APPLICATIONS

This is a 371 national phase application of PCT/EP2010/007075 filed Nov. 23, 2010, which claims priority from German Patent Application No. DE 10 2009 054 395.3, filed Nov. 24, 2009.

FIELD OF INVENTION

The present invention relates to a method for adapting threshold windows. The present invention further relates to a control device, a medical treatment apparatus, a medical monitoring apparatus, a digital storage means, a computer program product, and a computer program.

BACKGROUND OF THE INVENTION

Threshold windows for monitored medical measured variables are known from practice. In case the monitored medical measured variable exceeds the threshold window, a predetermined technical result as, for example, triggering an alarm, can be effected.

During the treatment of, e.g., a medical fluid, adaptation of threshold windows of measured variables can be necessary for several reasons. Those reasons include a drift or a permanent change of the absolute position of the measured variables due to uncritical reasons as, e.g., the mere positional change of a patient having his blood treated extracorporeally.

One object of the present invention is to propose another method for adapting threshold windows. Additionally, appropriate devices are proposed.

This object according to the present invention is achieved by a method for adapting threshold windows.

The method according to the present invention comprises adapting a second threshold window of at least a second, in particular medical, measured variable depending on or based on the change of a first threshold window of a first, in particular medical, measured variable. The adaptation is carried out by means of a control device which is provided and configured correspondingly.

Advantageous embodiments are included as subject matter of the dependent claims.

In the following description, terms like "can be" or "can have" etc. are intended to be understood as synonyms for "preferably is" or "preferably has" etc.

If, in the following, the terms first and second medical measured variables, threshold windows or the like are used, a person skilled in the art will recognize that those terms also include third, fourth or other medical measured variables, threshold windows or the like.

The term "medical measured variable" as used herein denotes a parameter or a characteristic or a state variable which relates to a patient.

A medical measured variable can relate to or be a parameter or a characteristic or a state variable which is considered upon assessing a clinical state or a change thereof.

The measured variable can be determined, qualified or quantified by detecting or measuring currently measured values, for example, by using appropriate detection and/or measurement devices such as sensors.

The terms "first measured variable" and "second measured variable" as used herein can refer to the same kind of measured variable, for example, a first and a second pressure measured variable. They can indicate an identical measured variable as, e.g., the same pressure, however, being measured twice with different sensors. The first and second measured variables can refer to different or differing measured variables as, for example, pressure and temperature.

One measured variable can be associated with another measured variable. For example, a second measured variable can depend on a first measured variable. However, this does not have to apply.

In the context of a treatment method, examples for medical measured variables can include physiological measured variables, in particular vital parameters of a patient, pressure, temperature, time and the like.

The term "patient" as used herein refers to a subject like a human or an animal independently of being healthy or ill.

The term "threshold window" as used herein refers to a range of values or an interval of values about or for a medical measured variable. The threshold window can comprise a range of measured values allowable for a measured variable or indicate or present an interval of values allowable for a measured variable.

A measured value of a measured variable which is detected to be within the threshold window can be regarded as allowable.

In the field of medicine or medicine technology, a threshold window can, for example, be understood as a limitation of a non-pathological scope or area.

Threshold windows can comprise an upper threshold or upper limit, respectively and/or a lower threshold or lower limit, respectively. Threshold windows can extend from a lower threshold to an upper threshold, or vice versa, wherein the (upper and/or lower) thresholds can or cannot be comprised in the range of values.

A threshold window can be a bilaterally or merely unilaterally limited range (e.g., having only an upper or a lower limit). Whenever the context of the present invention refers to a threshold window, the term is may also be understood as a threshold (for example, an upper threshold or a lower threshold).

Each measured variable can be assigned one or several threshold windows.

The term "adapting" or "adaptation" of a threshold window as used herein refers to a change or offset or adjusting of the range of thresholds of a medical measured variable due to a change of a first medical measured variable or of the threshold window thereof.

The threshold window can be adapted relative to the currently measured value of each measured variable.

Preferably, the threshold window is adapted only after a previous confirmation by a user.

The term "control device" as used herein refers to a device being designed, configured and/or provided for effecting or triggering an adaptation of the second threshold window depending on a change of a first threshold window.

The control unit can be embodied to allow an automation or an automatic or automated performance of the method according to the present invention.

This can advantageously contribute to reducing the effort necessary for adapting the threshold windows.

The control device can induce or effect the performance of all or substantially all method steps. The method according to the present invention can substantially or entirely be performed by the control device. The method can be performed in part by the control device.

In a preferred embodiment, the second threshold window can be adapted by actuating only one actuation device provided for activating the control device.

The actuation or activation of the control device can be effected by pushing, rotating, switching, tipping, touching etc. of the actuation device.

Appropriate actuation devices include a knob, a key, a soft key, a hard key, a switch, a controller, a button of a touch pad, a button of a touch screen, a button which can be actuated or activated by means of an external input device like a keypad, a mouse, a pen and the like, a speech input device and the like.

The actuation can preferably consist of a unique or one-time actuation, respectively, i.e., a unique pushing, tipping, touching etc.

The control device can be activated or actuated by a user as, for example, clinic staff, e.g., physicians, nursing staff and the like. The adaptation of the threshold windows is preferably effected by an authorized person.

The control device can be activated via signal transmission by means of another device.

In a further preferred embodiment, the method according to the present invention comprises setting or determining a characteristic of at least one threshold window of a medical measured variable.

The term "characteristic" of a threshold window as used herein refers to a position or an extension of the threshold window, a spatial appearance of, e.g., a two-dimensionally presented range of values, etc., in relation to a predetermined value of the measured variable, respectively.

The threshold window can encompass values above such a (predetermined) value of the measured variable and/or values below the value of the measured variable.

The threshold window can be arranged symmetrically or asymmetrically about such a predetermined value of the measured variable, for example, about or around an initial value of the medical variable that could be found at the beginning of a treatment.

The predetermined value of the measured variable can be a reference value for the threshold window or for the characteristic thereof.

The characteristic of the threshold window can indicate a relative position, relative to a predetermined or detected basic value of the measured variable or to a detected initial value of the measured variable or to an expected value of the measured variable or to an otherwise predetermined or detected value of the measured variable.

The characteristic of the threshold value can be or is individually set for a patient relative to an initial measured value of a medical measured variable at the beginning of a treatment.

Alternatively, it is possible to change the characteristic of a threshold window or of some or all threshold windows during the treatment. This can, for example, manually be effected by a user, for example, by actuating a luffing key for up- or downregulating of single values or ranges of values. This way, post-adapted or post-set threshold values or threshold windows can be used as a basis for the adaptation of the second threshold window according to the present invention.

The characteristic can be a width or a height of the threshold window relative to an individual measured value of the measured variable or relative to a predetermined value.

The term "width or height of the threshold window" as used herein refers to an extension of the threshold window from a lower threshold of the medical measured variable to an upper threshold of the medical measured variable.

Alternatively, or additionally, the characteristic can be an interval between an upper threshold and/or between a lower threshold and the initial measured value of the medical measured variable.

The characteristic of the threshold window or threshold windows of one or several measured variables can, for example, be predetermined or assessed in the so called settings of a medical treatment apparatus.

Presettings for each threshold window having been deposited in the settings can be consulted or used for adapting the threshold windows. This can preferably be effected automatically by means of a control device.

The presettings of all threshold windows to be adapted can be identical. However, the presettings can also differ.

The object of the present invention is further achieved by a control device. All advantages achievable by means of the method according to the present invention can likewise undiminishedly be achieved by the control device according to the present invention.

The control device of the present invention is provided and configured to be activated or controlled, respectively, in order to adapt a second threshold window of at least a second medical measured variable depending on or based on, respectively, the change of a first threshold value of a first medical measured variable in case of such a change.

The control device of the present invention can be provided and configured to be activated in order to perform a method according to the present invention.

The control device of the present invention can be provided and configured to be activated by a user by actuating only one (single) actuation device.

The object of the present invention is further achieved by a medical treatment apparatus and/or by a medical monitoring apparatus. All advantages achievable by means of the method according to the present invention can likewise be undiminishedly achieved by the medical treatment apparatus and/or the medical monitoring apparatus according to the present invention.

The medical treatment apparatus and/or the medical monitoring apparatus according to the present invention comprise at least one control unit according to the present invention.

The medical treatment apparatus of the present invention and the medical monitoring apparatus of the present invention can be provided and used as separate units. However, they can also be connected to each other. In particular, the monitoring apparatus can be part of the treatment apparatus. The present invention encompasses all those possibilities mentioned above.

The medical treatment apparatus and/or the medical monitoring apparatus can (each) comprise and/or be connectable to other device like measurement and/or detection devices, input or output devices, storage means and the like.

The medical treatment apparatus and/or the medical monitoring apparatus can in particular comprise at least one actuation device. The actuation device can be provided and designed for facilitating an activation of the control device. Such an activation can, for example, be achieved or induced by one-time actuating the actuation device.

According to an embodiment of the present invention, the one-time actuation of the actuation device can be confined to a single or one-time keystroke.

The medical treatment apparatus according to the present invention is preferably suited for an extracorporeal blood treatment like, for example, dialysis, hemofiltration, hemodiafiltration, apheresis, adsorption, blood oxygenation and the like. The medical treatment apparatus according to the present invention can be a cardiopulmonary apparatus.

In a preferred embodiment, the medical treatment apparatus is a blood treatment apparatus for the extracorporeal treatment of blood by means of at least one of the methods comprising hemodialysis, hemodiafiltration and/or therapeutical apheresis.

The medical treatment apparatus according to the present invention can be an apparatus for performing a peritoneal dialysis.

The medical monitoring apparatus can be designed and provided or configured for monitoring the performance of a medical treatment process, for example, of one of the treatment methods mentioned above.

The object of the present invention is further achieved by a digital storage means and/or a computer program product and/or a computer program. All advantages achievable by means of the method of the present invention can likewise undiminishedly be achieved by these means.

The digital storage means, which is in particular a disc, CD or DVD, preferably features electrically readable control signals which are able to interact with a programmable computer system such that the automatically performable steps of the method according to the present invention will be executed.

Thereby, all, a few or some of the automatically performable steps of the method according to the present invention can be induced. The latter also applies for the computer program product and the computer program.

The computer program product preferably comprises a program code stored on a machine readable medium for executing a method according to the present invention when executing the program product on a computer.

The term "machine readable data medium" as used herein refers to a medium containing data or information being interpretable by software and/or hardware. The medium can be a data medium like a disc, a CD, DVD and the like.

The computer program comprises a program code for executing the automatically performable steps of the method according to the present invention when executing the program on a computer.

The method according to the present invention can advantageously serve for facilitating the adaptation of threshold windows. Thus, it can, for example, advantageously be possible to offset a plurality of threshold windows at the same time.

The use of the control device can advantageously contribute in updating the medical measured variables detected in or during a treatment in a simple and less complex manner.

The present invention can, therefore, permit a simpler usability and/or operability of a medical treatment apparatus. It can thus advantageously be possible to save time and costs.

Additional advantages include the less possible appearance of false alarms. Furthermore, there is less possibility of omitting the required adaptation of a threshold window for a second, third or another measured variable and to thus optionally risk an undesired process routine like an automatic termination of a treatment function.

It should hereby be emphasized that the adaptation is preferably not effected without any user action; the user must preferably interact in order to affirm or initiate that an adaptation of the second or other threshold window may take place. In such a way, it can advantageously be avoided to miss a change—in particular of a relevant measured variable—that may be decisive or relevant.

According to the present invention, the threshold windows are offset or adapted, respectively, by means of the control device—preferably after affirmation by the authorized user. Therefore, for example, an alarm (e.g., a pressure alarm) is not triggered only when a second measured value infringes the end of the scale or exceeds a second threshold value which is possibly not valid any more. The new values, pressures, alarm limits can be offset or adapted, respectively, automatically "throughout the system." It is therefore possible that the user is informed earlier and thus correctly about an infringement of the end of the scale by means of a notification or of an alarm.

According to the present invention, by means of this relatively early notification in case of an infringement of the end of the scale or a value exceeding beyond the threshold value, respectively, the user can take more actions than with known systems. According to the present invention, for example, in case of monitoring medical measured variables during a blood treatment, there can advantageously remain enough time for action when considering the pre-filter pressure as indicator for clotting in the filter. Thus, the treatment does not have to be terminated due to a lack of time for responding or for taking action; rather, different measures can still be taken.

Thus, when adequately embodied, the present invention behaves like an "early warning system" such that the user can take the required measures like, e.g., changing from postdilution to predilution or adapting the anticoagulation at an early stage of time before these measures could not be taken any longer. That way, the lifetime of the filter can be increased. Thus, the present invention can provide economic advantages.

BRIEF DESCRIPTION OF THE DRAWINGS

The present invention is in the following illustrated by way of example with reference to the appended drawing, wherein.

DETAILED DESCRIPTION OF THE DRAWINGS

Figure 1:
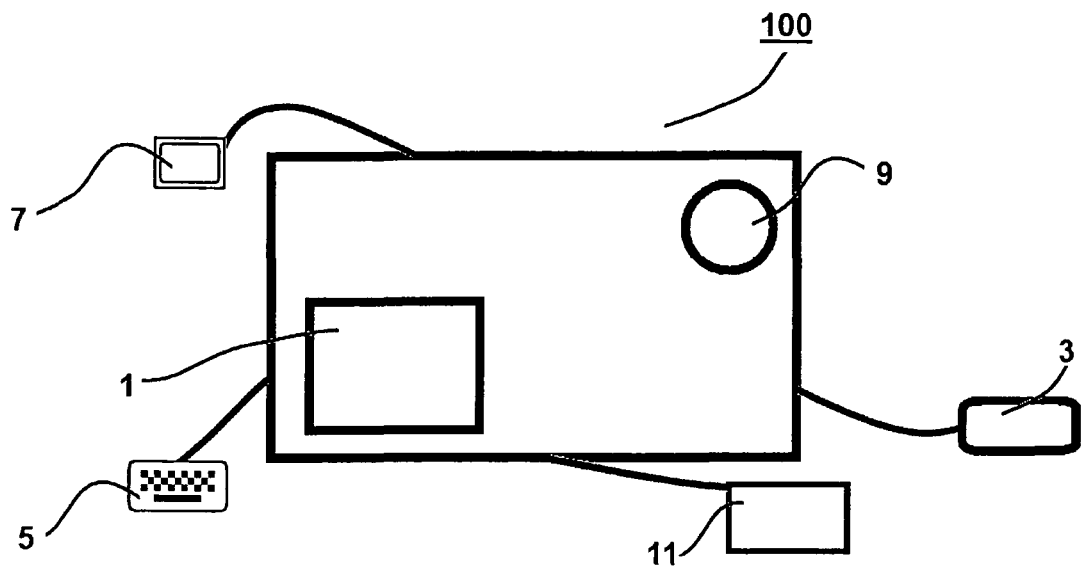
FIG. 1 shows a schematic arrangement of a medical treatment apparatus according to the present invention.

FIG. 1 shows a largely schematic arrangement of the medical treatment apparatus 100 according to the present invention.

The medical treatment apparatus 100 comprises a control unit 1.

The medical treatment apparatus 100 comprises a detection device 3 like, for example, a pressure sensor.

The medical treatment apparatus 100 comprises an input device 5, for example, a keypad, and an output device 7, for example, a monitor.

The medical treatment apparatus 100 comprises an actuation device 9.

The medical treatment apparatus 100 comprises a monitoring apparatus 11.

As shown in FIG. 1, the monitoring apparatus 11 can be part of the medical treatment apparatus 100. However, according to the present invention, the monitoring apparatus 11 can also be used as a separate unit not being part of any treatment apparatus.

Figure 2:
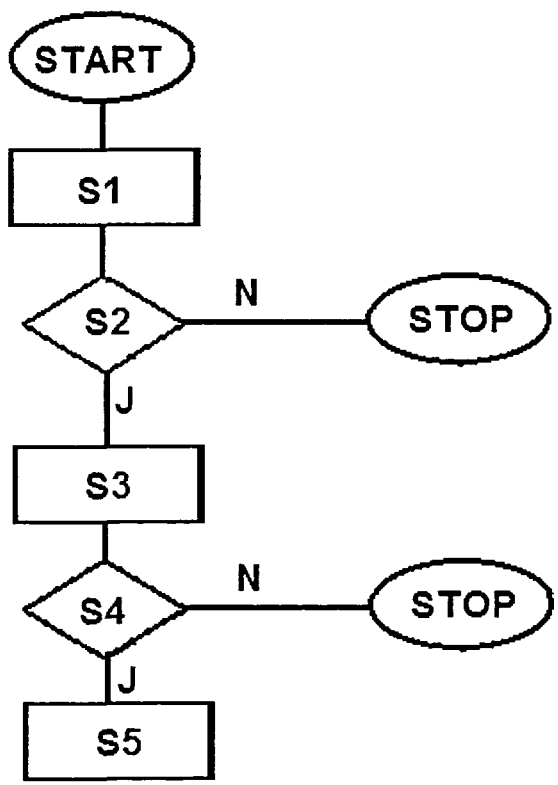
FIG. 2 shows a flow diagram of a method according to the present invention.

FIG. 2 schematically shows a flow diagram of a method according to the present invention for adapting a second threshold window depending on a change of a first threshold window.

For easier understanding the co-operation of the single components, reference is made to the arrangement shown in FIG. 1. The components involved in the method according to the present invention are for this reason denoted with the reference numerals of FIG. 1 though they are not necessarily shown in FIG. 2, too.

At the beginning of a treatment, in step S1, a characteristic of the threshold windows is set for the measured variables which are relevant during the treatment—this is preferably done individually for each patient. The characteristic can, however, also be known before and optionally be looked up.

Hereto, the user can input the characteristic of the threshold window of a medical measured variable at issue, e.g., in form of numeric values, into the medical treatment apparatus 100 by means of the input device 5. The threshold windows can be stored in the settings of the medical treatment apparatus 100, for example, in an appropriate storage means.

The assessment of threshold windows can be a step of the present invention; however, the assessment is not an essential or indispensable, respectively, part of the method of the present invention. As mentioned above, appropriate threshold windows which have, e.g., previously been deposited in the settings can be used.

Instructions or requests for the user can be presented by means of the output device 7.

During the treatment, a measurement or detection device 3 detects at least one measured variable relevant for the treatment. The control device 1 and/or the user can now study the actual values of the first measured variable and decide based on them if an adaptation of the threshold window of the first measured variable would be helpful or necessary.

In case a change of a first threshold window of a first measured variable, for example, the venous pressure during a dialysis treatment, is necessary, the user may change the first threshold window correspondingly. Optionally, the user can accept a proposal of the control device by means of confirmation.

To this end, in step S2, the user can first be requested if he wants to change the first threshold window.

If this is not the case ("N" for NO), the method according to the present invention can be terminated ("STOP").

If the user wants to adapt the first threshold window ("J" for YES), he can change a characteristic of the first threshold window, for example, a width, an interval between an upper threshold and/or a lower threshold and the initial measured value of the first measured variable and the like.

Subsequently, the user can check and confirm the changes he made. If the adaptations were not correct and/or not desired or turned out as unnecessary, the user can reset the threshold window to its original value or its original characteristic, respectively.

Suitable input and/or confirmation devices can be provided correspondingly.

Preferably, since the user has to confirm the adaptation of the first threshold window, it can advantageously be avoided that the threshold windows is adapted in an uncontrolled manner and to thus optionally miss a decisive change of the first measured variable.

Upon request, the user decides in step S4 if he wants to automatically adapt the second threshold window of the second measured variable, for example, of the transmembrane pressure, and optionally further threshold windows.

The settings necessary for offsetting or adapting the threshold windows can be deposited in the settings of the medical apparatus. The values concerning the size and/or the position of the threshold window can be maintained or changed individually. Thus, it can, for example, be possible to maintain a relative position of the threshold window relative to the measured value which has been identified to have triggered the adaptation.

Thus, in step S4, the user can advantageously be given the possibility to newly position the threshold windows of all medical measured variables, e.g., of all pressure measurement variables, at the same time.

If the user does not want to adapt the threshold windows ("N" for NO), the method can be terminated ("STOP").

If the user wants to adapt the threshold windows ("J" for YES), in step S5 he can activate the control device 1 by means of actuating the actuation device 9 in order to effect or induce an adaptation of the second and optionally further threshold windows.

What is claimed is:

1. A blood treatment apparatus comprising:
   a control device which is programmed to perform a computer-implemented method for adapting threshold windows of medical measured variables, each of the threshold windows comprising a respective upper threshold limit value and a respective lower threshold limit value;
   an actuation device configured to activate the control device;
   a detection device for detecting a first measured variable; and
   an alarm that the control device is configured to trigger when any of the medical measured variables are outside of their respective threshold windows,
   wherein the method for adapting threshold windows of medical measured variables comprises:
      detecting, via the detection device during a blood treatment, the first measured variable;
      changing, via user input manually entered by a user into an input device of the blood treatment apparatus during the blood treatment, a first threshold window of the first measured variable, the first threshold window comprising at least one of a range of values and an interval of values; and
      changing, by the control device automatically during the blood treatment and in response to the changing of the first threshold window, a second threshold window of a second measured variable, wherein the changing of the second threshold window includes changing both an upper threshold limit value and a lower threshold limit value of the second threshold window to new values that are based on the changed first threshold window of the first measured variable, the first measured variable being different from the second measured variable.

2. The medical treatment apparatus according to claim 1, wherein the changing of the first threshold window of the first measured variable occurs via the user input in response to information presented to the user via an output device of the blood treatment apparatus.

3. The medical treatment apparatus according to claim 1, wherein the control device is configured to be activated responsive to user input via the actuation device.

4. The medical treatment apparatus according to claim 1, wherein the first or the second variable is equal to venous pressure.

5. The medical treatment apparatus according to claim 1, wherein the first or the second variable is equal to transmembrane pressure (TMP).

6. The medical treatment apparatus according to claim 1, further comprising the step of setting or determining a characteristic of at least one threshold window of a measured variable.

7. The medical treatment apparatus according to claim 6, wherein the characteristic of the threshold window is set in relation to an initially measured value of the measured variable for a first patient at the beginning of a treatment for said first patient.

8. The medical treatment apparatus according to claim 7, wherein the characteristic is a relation between a width of the threshold window and either a predetermined value or an initially measured value of the measured variable.

9. The medical treatment apparatus according to claim 7, wherein the characteristic corresponds to at least one interval selected from the group consisting of: an interval between an upper threshold and a predetermined value, an interval between a lower threshold and a predetermined value, an interval between an upper threshold and the initially measured value of the measured variable, and an interval between a lower threshold and the initially measured value of the measured variable.

10. The medical treatment apparatus of claim 1, wherein the control device is configured to be activated by a unique actuation of only the actuation device by the user.

11. The medical treatment apparatus according to claim 10, wherein the blood treatment apparatus is for treating blood by at least one method selected from the group consisting of: hemodialysis, hemofiltration, hemodiafiltration, and therapeutical apheresis.

12. A non-transitory computer-readable storage medium with an executable program stored thereon, wherein the program instructs a programmable computer system of a blood treatment apparatus comprising: (i) a control device, (ii) an actuation device configured to activate the control device, (iii) a detection device, and (iv) an alarm, to execute a method for adapting threshold windows of medical measured variables during a blood treatment, each of the threshold windows comprising a respective upper threshold limit value and a respective lower threshold limit value, the method comprising the steps of:

detecting, via the detection device, a first measured variable;

changing, via user input manually entered by a user into an input device of the blood treatment apparatus during the blood treatment, a first threshold window of the first measured variable, the first threshold window comprising at least one of a range of values and an interval of values; and changing, by the control device automatically during the blood treatment and in response to the changing of the first threshold window, a second threshold window of a second measured variable, wherein the changing of the second threshold window includes changing both an upper threshold limit value and a lower threshold limit value of the second threshold window to new values that are based on the changed first threshold window of the first measured variable, the first measured variable being different from the second measured variable.

* * * * *